United States Patent
Fatemi (10) Patent No.: US 6,709,407 B2
(45) Date of Patent: Mar. 23, 2004

(54) METHOD AND APPARATUS FOR FETAL AUDIO STIMULATION

(75) Inventor: Mostafa Fatemi, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 56 days.

(21) Appl. No.: 10/016,250

(22) Filed: Oct. 30, 2001

(65) Prior Publication Data

US 2003/0083595 A1 May 1, 2003

(51) Int. Cl.⁷ .................................................. A61B 5/00
(52) U.S. Cl. ........................ 600/559; 600/437; 73/585; 381/151
(58) Field of Search ................................ 600/437, 443, 600/552, 559, 591, 27, 28; 128/897, 898; 381/301, 312, 326, 332, 333, 385, 388, 151; 73/585

(56) References Cited

U.S. PATENT DOCUMENTS

| | | | |
|---|---|---|---|
| 4,798,539 A | 1/1989 | Henry et al. | |
| 5,033,968 A | 7/1991 | Hecht | |
| 5,420,581 A | 5/1995 | Peters et al. | |
| 5,491,756 A | 2/1996 | Francais | |
| 5,764,776 A | * 6/1998 | Francais | 381/300 |
| 5,873,736 A | * 2/1999 | Harrison | 434/322 |
| 5,885,225 A | * 3/1999 | Keefe et al. | 600/559 |
| 5,913,834 A | 6/1999 | Francais | |
| 5,921,928 A | 7/1999 | Greenleaf et al. | |
| 5,991,239 A | 11/1999 | Fatemi-Booshehri et al. | |
| 6,169,814 B1 | 1/2001 | Johnson | |
| 6,556,861 B1 | * 4/2003 | Prichep | 600/544 |
| 6,631,197 B1 | * 10/2003 | Taenzer | 381/316 |

* cited by examiner

Primary Examiner—Charles Marmor
(74) Attorney, Agent, or Firm—Quarles & Brady LLP (57) ABSTRACT

The present invention is a method and apparatus for applying a focused, directed audio beam at a fetus to stimulate the fetus in utero. An ultrasound signal is amplitude modulated with an audio range signal, and directed to an ultrasound transducer positioned on the abdomen of a pregnant woman. A focused beam from the ultrasound transducer is directed at the head of a fetus, wherein the resultant audio signal stimulates the middle ear, causing the fetus to move. Motion of the fetus can be tracked to test hearing in individual ears or to test the general health of the fetus. Furthermore, the focused beam can be successively directed at the fetus to cause to the fetus to move to a selected location in the womb for clinical testing or delivery.

21 Claims, 8 Drawing Sheets

METHOD AND APPARATUS FOR FETAL AUDIO STIMULATION

TECHNICAL FIELD

The present invention relates to fetal stimulation and testing devices, and more specifically to an ultrasound device for stimulating a fetus in utero and for monitoring movement of the fetus as a result of the stimulation.

BACKGROUND

Audio fetal stimulators are commonly used in clinics to evaluate both the general health and hearing of fetuses in utero. Audio stimulation devices can include both artificial larynxes and devices which employ speakers to "communicate" with the fetus, such as those described in U.S. Pat. Nos. 6,169,814 and 5,913,834. In each of these devices, an audio sound source is generated externally and is transmitted into the abdominal cavity of the mother to stimulate the fetus. Movement of the fetus can be monitored to track reaction to the audio stimulation, and therefore to verify general hearing, assess fetal health based on response to the stimulation, and to analyze other parameters.

While these audio stimulation devices are useful for general testing of both the overall hearing and response of the fetus, there are certain limitations associated with audio stimulation devices of the type described above. These devices, for example, produce sound which is transmitted to the abdominal cavity with little or no directivity. Because the audible sound has very long wavelengths, it tends to spread equally in all directions in the abdomen. Therefore, when audio stimulation is applied to test hearing, the sound is transmitted simultaneously to both fetal ears. It is not possible to test each of the ears individually. Furthermore, although the sound stimulation causes the fetus to move, prior art methods are not designed to cause the fetus to move to a particular position or location in the uterus. Because the sound is almost non-directional, there is no "quiet" place in the uterus at which the fetus would feel less stressed. Hence the fetus moves almost randomly to the audio stimulation.

SUMMARY OF THE INVENTION

The present invention is a method and apparatus for audio stimulation of a fetus in utero. The fetal stimulator of the present invention produces fetal auditory stimulation by direct conversion of ultrasound energy to audible sound waves. Hence the fetal stimulator of the present invention can be used to stimulate the fetus in a very specific region.

In the present invention, a focused ultrasound transducer is driven by an amplitude-modulated signal to provide localized, directed energy to the fetus. An RF generator provides a carrier signal at the ultrasound frequency, between 1 and 10 MHz, and an audio a modulation generator provides a modulation signal. An amplitude modulator modulates the carrier signal with the audio signal to produce a modulated signal. The resultant modulated signal is used to drive the ultrasound transducer. The transducer, which is positioned on the abdomen of the mother, produces a single focused beam which can be aimed at the fetal head, the ear, or other selected location.

Movement of the fetus can be monitored in a number of known ways, movement can be monitored, by the mother, which provides an indication when she senses fetal movement. Alternatively, fetal movement can be monitored by a Doppler fetal monitor, through analysis of Doppler shift data from applied and received signals, and by synchronization to a heart beat of the fetus. The fetal stimulator described above can be applied in a number of different clinical applications, and is particularly suited for use in assessment of the hearing and general health of a fetus.

It is an object of the invention to provide a method and apparatus for selectively applying a highly localized, highly directive, and calibrated energy beam to a fetus.

It is another object of the invention to provide a method and apparatus for monitoring motion of a fetus in conjunction with the application of a highly localized, highly directive ultrasound beam.

It is yet another object of the invention to provide a method and apparatus for individually testing the hearing in each of the ears of a fetus in utero.

It is still another object of the invention to provide a method and apparatus for repositioning a fetus in the womb.

It is yet again another object of the invention to provide a method and apparatus for testing the general health of a fetus.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DETAILED DESCRIPTION OF THE PREFERRED EMBODIMENTS

When ultrasound interacts with an object, a small radiation force is exerted on that object as a result of momentum change by such interaction. For an ultrasound beam with the total power of P, this force is given by $F=P/c$, where c is the speed of sound in the medium. For an amplitude modulated ultrasound beam with the amplitude $U(t)=U_0 \cos(\Delta \omega t^2)\cos(\omega_0 t)$, the resulting force will be in the form of $F(t)=F_0+F_0$ Cos($\Delta\omega t$)/$^4$. This force vibrates the object at frequency $\Delta\omega$. If the frequency $\omega$ is selected to be in the audio range, and the beam is directed to the structures in the middle ear, for example, a sound at this frequency is heard. When the beam is directed at a fetus in utero, the beam can be used to stimulate the fetus and cause the fetus to move. Furthermore, the motion of the fetus can be monitored to test hearing and to provide a general health assessment of the fetus.

Figure 1:
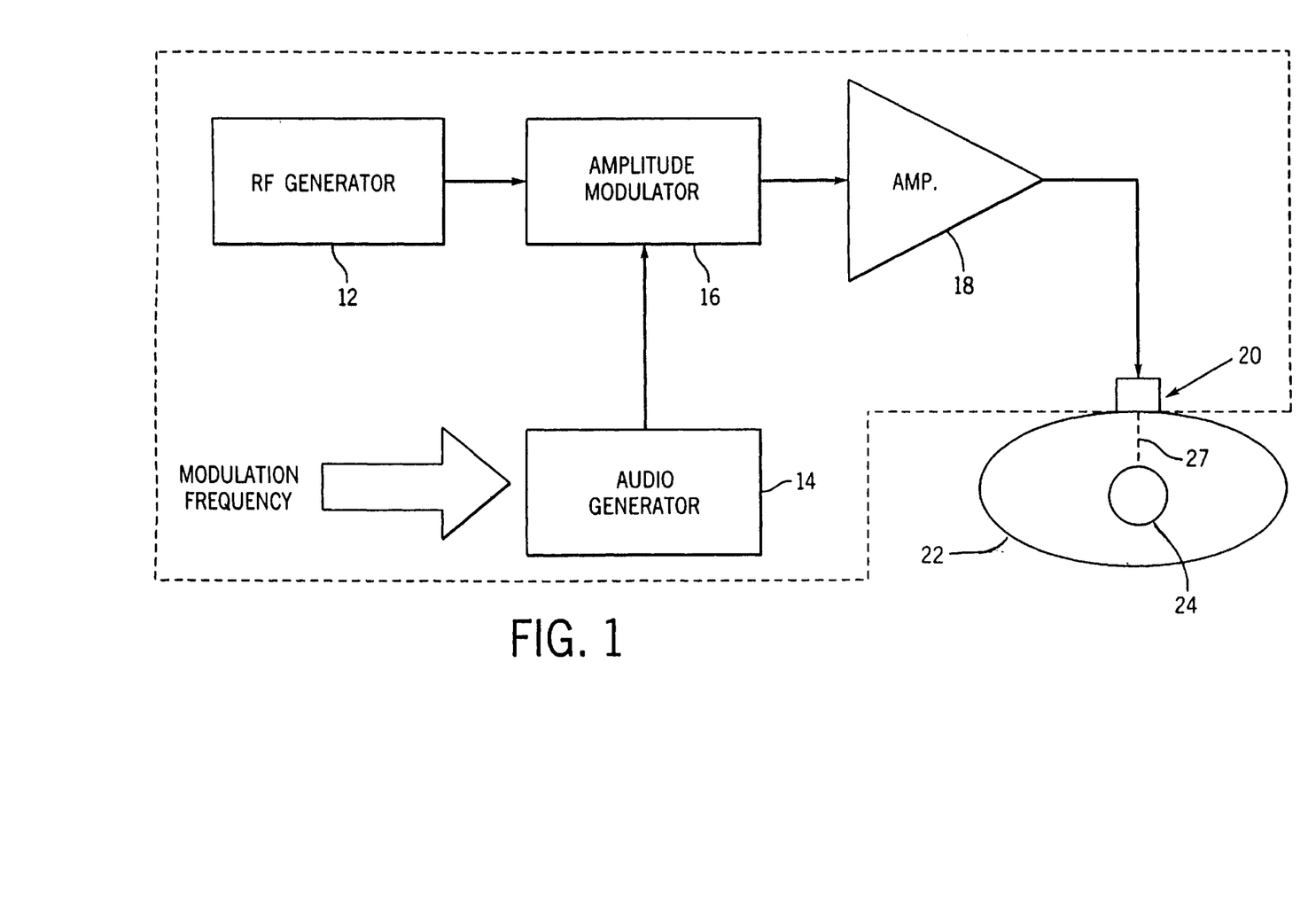
FIG. 1 is a block diagram of a fetal audio stimulator constructed in accordance with one embodiment of the invention.

Referring now to the figures and more particularly to FIG. 1, a first embodiment of an ultrasound signal generator or fetal audio stimulator 10 for generating an ultrasound beam as described above is shown. The fetal audio stimulator 10 comprises an RF generator 12, audio generator 14, amplitude modulator 16, amplifier 18 and ultrasound transducer 20. The RF generator 12 provides a carrier signal in the ultrasound frequency between 1 and 10 Mhz and the audio generator 14 provides a modulation signal whose frequency is in the audio range. The carrier signal from the RF generator 12 and the audio signal from the audio generator 14 are each directed to the amplitude modulator 16, which amplitude modulates the carrier signal with the audio signal, preferably by using a double side band suppressed carrier method to produce a modulated output signal. The modulated output signal is in turn directed to the amplifier 18, which amplifies the signal to a predetermined level. The amplified signal is then directed to the ultrasound transducer 20 which produces a single focused output beam 27. In use the ultrasound transducer 20 is positioned on or coupled to an abdomen 22 of a mother carrying a fetus, and the beam 27 is directed at the head 24 of the fetus, and preferably at the ear of the fetus. The beam 27 produces a force which vibrates the head of the fetus 24 or a portion thereof at the audio frequency established by the audio generator 14.

Figure 2:
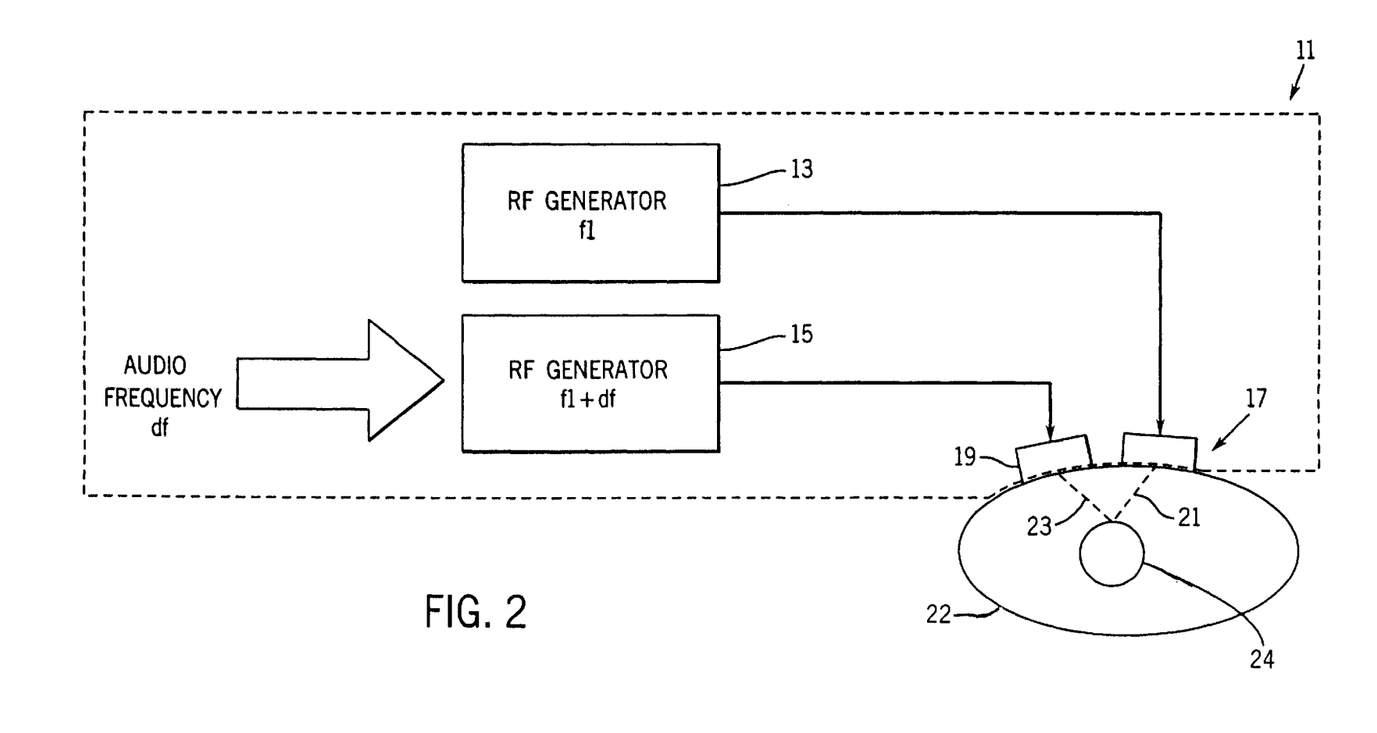
FIG. 2 is a block diagram of a fetal audio stimulator constructed in accordance with a second embodiment of the invention.

Referring now to FIG. 2 an audio ultrasound signal generator or fetal audio stimulator 11 constructed in accordance with a second embodiment of the invention is shown. The fetal audio stimulator 11 comprises a first RF generator 13 providing a continuous wave signal at a first frequency f1 and a second RF generator 15 providing a continuous wave signal at a frequency f1 plus df, where df is an audio frequency that can be adjusted by the user. The RF generator 13 drives a first ultrasound transducer 17 while the RF generator 15 drives a second ultrasound transducer 19. Each of the ultrasound transducers 17 and 19 are positioned on or coupled to an abdomen 22 of a mother carrying a fetus. Each of the ultrasound transducers 17 and 19 produce a focused beam 21 and 23, respectively, which is directed at the head 24 of the fetus. In this application the stimulation site is located at about the intersection of the focal points of the two focused beams 21 and 23, where a "beat" force is generated at a frequency df. The generation of this force is described more fully in U.S. Pat. No. 5,991,239 which is hereby incorporated by reference. The use of the intersection of two beams 21 and 23 allows the stimulation to be aimed at a specific location with a higher degree of precision than the use of the single beam, described above. Furthermore, this method confines the resultant beam force mainly to the intersection region.

Referring now to FIGS. 3–6, four embodiments of clinical testing devices comprising a signal generator or fetal audio stimulator 10 and associated monitoring device are shown. Each of these devices comprise a fetal audio stimulator 10, and a monitor device comprising a motion detector and/or an event tracker. These devices can be used for stimulating a fetus and tracking resultant responses, and are useful in clinical situations as described below.

Figure 3:
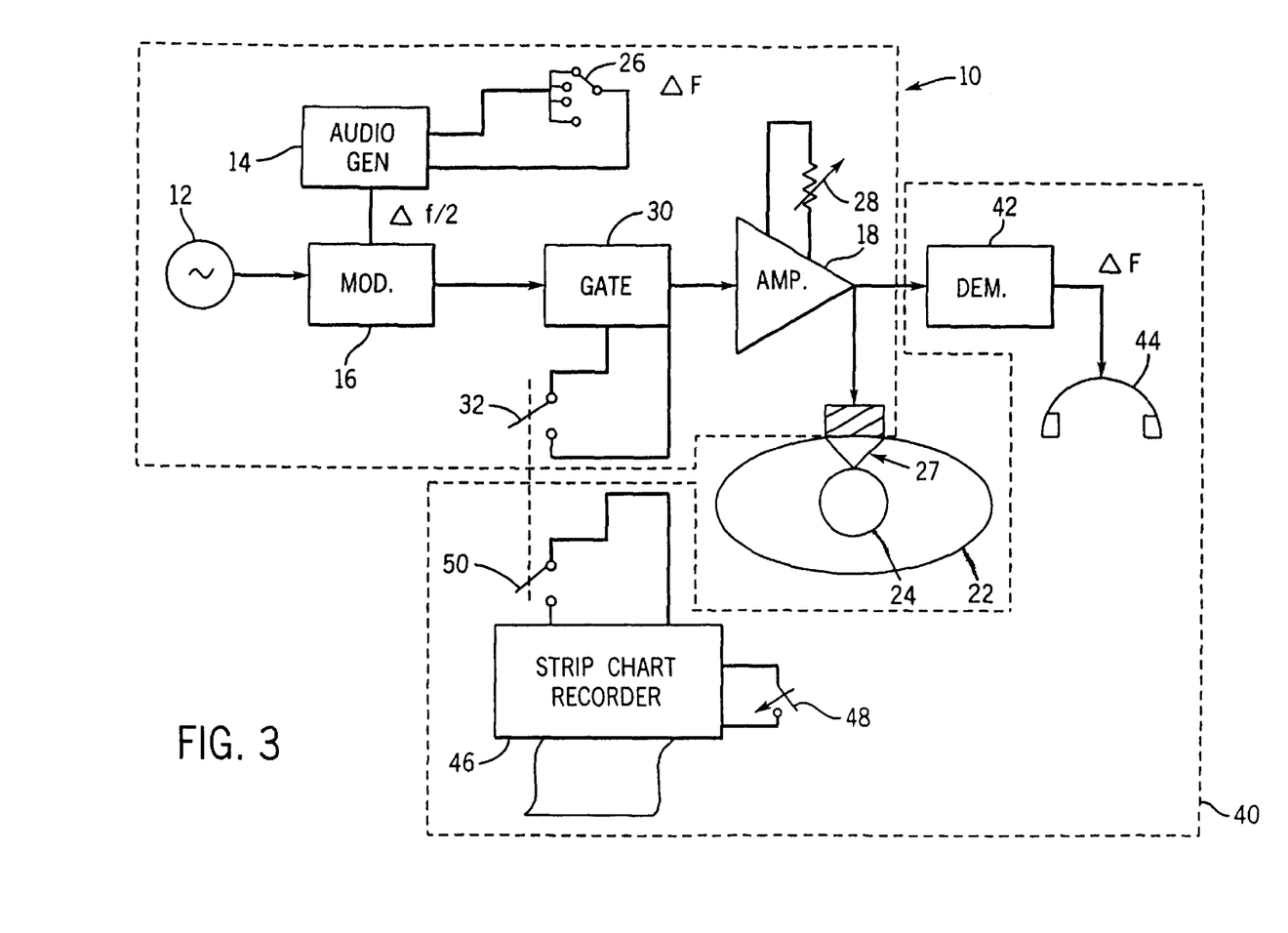
FIG. 3 is a block diagram of a fetal audio stimulator and associated monitoring device constructed in accordance with another embodiment of the invention.

Referring now specifically to FIG. 3, a fetal audio stimulator 10 is shown in use in conjunction with an event tracker or monitoring device 40. The fetal audio stimulator 10 of FIG. 3 is constructed as described with reference to FIG. 1 above. The fetal audio stimulator 10 of FIG. 3, however, further includes a frequency selector 26 allowing a physician or other user to select between a number of audio frequencies. The frequency selector 26 is graduated in terms of different values of $\Delta f$. An amplitude control 28 shown as comprising a potentiometer in a feedback loop of the amplifier 18, allows a user to select an amplification level for the amplitude modulated signal directed to the ultrasound transducer 20. The fetal audio stimulator 10 further comprises a gate 30 selectively activated by gate control switch 32 allowing a physician or other user to selectively apply the amplitude modulated signal to the amplifier 18, thereby controlling the duration of the application of the beam 27 to the head 24 of the fetus.

The event tracker or monitoring device 40 is a mother-controlled monitor. The monitoring device 40 comprises an envelope detecting demodulation circuit 42 for demodulating the amplitude modulated signal provided to the ultrasound transducer 20, thereby recovering the audio sound generated by the radiation force of ultrasound, i.e., the selected frequency $\Delta f$. The demodulated signal is provided to an earphone 44 which can be worn by the mother to detect when a beam 27 has been applied to the head 24 of the fetus. A strip chart recorder 46 records an event when a mother or other user detects motion of the fetus and activates a first marker switch 48, and also by the marker switch 50 when the gate-controlled switch 32 is activated by the physician to apply the amplitude modulated signal to the ultrasound transducer 20. Therefore, the chart records each application of sound to the fetus (marker switch 50) and any subsequent fetal movements as recorded by the mother (marker switch 48).

Figure 4:
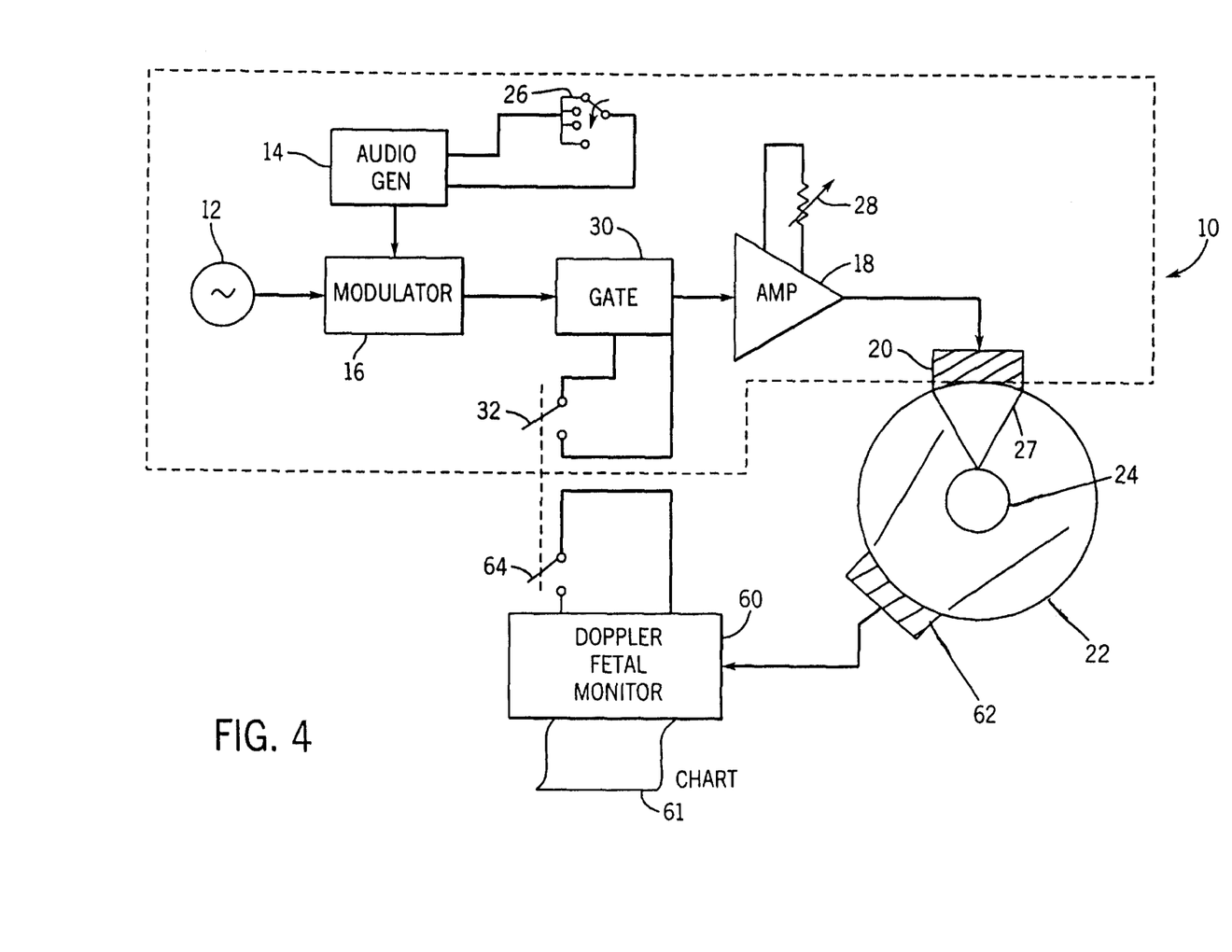
FIG. 4 is a block diagram of a fetal audio stimulator and associated monitoring device constructed in accordance with another embodiment of the invention.

Referring now to FIG. 4 a second embodiment of a monitoring device is shown. In this embodiment the event tracker or monitoring device comprises a low power ultrasound Doppler fetal monitor 60 coupled to a fetal monitor probe 62 which is positioned on or coupled to the abdomen 22 of the mother. In this application, the ultrasound frequency of the probe 62 can be different from that of the ultrasound transducer 20, and the beam of the monitor probe 62 is preferably less focused than that of the ultrasound transducer 20, so it can detect fetal motion within a wide field of view. The Doppler monitor 60 further includes an event recorder 61 which records both fetal motion and each application of ultrasound introduced to the fetal ear, as indicated. Events can be recorded on a paper chart or stored in a digital memory associated with the event recorder 61. The user can therefore evaluate fetal motion resulting from each stimulation applied to the fetal head or ear. The Doppler monitor 60 can be selectively activated by a switch 64.

Figure 5:
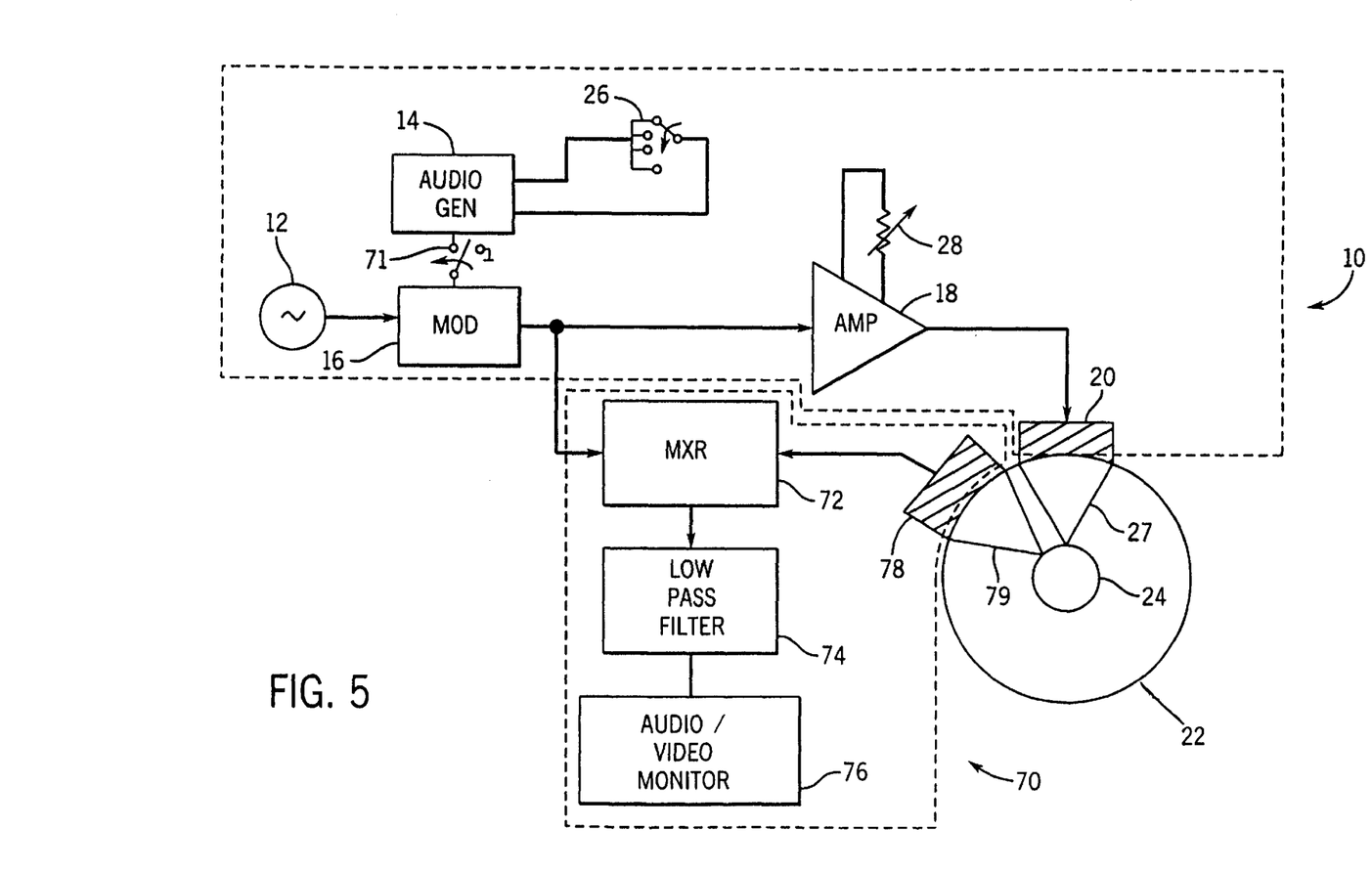
FIG. 5 is a block diagram of a fetal audio stimulator and associated monitoring device constructed in accordance with another embodiment of the invention.

Referring now to FIG. 5 a third embodiment of a fetal audio stimulator 10 and associated event tracker of monitoring device 70 are shown. In this embodiment, the ultrasound source that is used for stimulating the fetus is also used for fetal motion detection, thereby allowing for direct detection of motion of the body region exposed to stimulation. Here again the fetal audio stimulator 10 is constructed basically as described with respect to FIG. 1. In this embodiment, however, a physician controlled switch 71 is positioned between the amplitude modulator 16 and the audio generator 14 thereby allowing a physician or other user to selectively apply an audio signal to the amplitude modulator 16, allowing the physician to produce audio sound in the fetal hearing system whenever he wishes and for any duration.

The monitoring device 70 comprises a downmixer 72 and associated receiving transducer 78, which receives reflected ultrasound signals 79 from the fetal head 24. The ultrasound transducer 20 and receiving transducer 78 are located in proximity to each other and are each directed at the same region of the head 24 of the fetus. Furthermore, the center frequency receiving transducer 78 is selected to be substantially the same as that of the ultrasound transducer 70. The mixer circuit 72 receives an amplitude modulated signal from the amplitude modulator 16, and a reflected signal from the receiving transducer 78, and downmixes these two signals. The output of the mixer circuit 72 is coupled to a low pass filter 74 which receives and filters the down-mixed signal to detect a Doppler shift in the frequency of the reflected ultrasound field indicative of whether fetal motion has occurred. From the low pass filter this signal is passed to an audio-video monitor 76 which produces a signal indicative of the Doppler shift described above. This unit can display the Doppler shift by a video (CRT) monitor, or can use an audio device such as a speaker. In this application, the monitoring device 70 can detect motion when the switch 71 is in the On or Off position. However, because the Doppler shift is different when the switch 71 is at On or Off position, the resultant signals can be differentiated.

Figure 6:
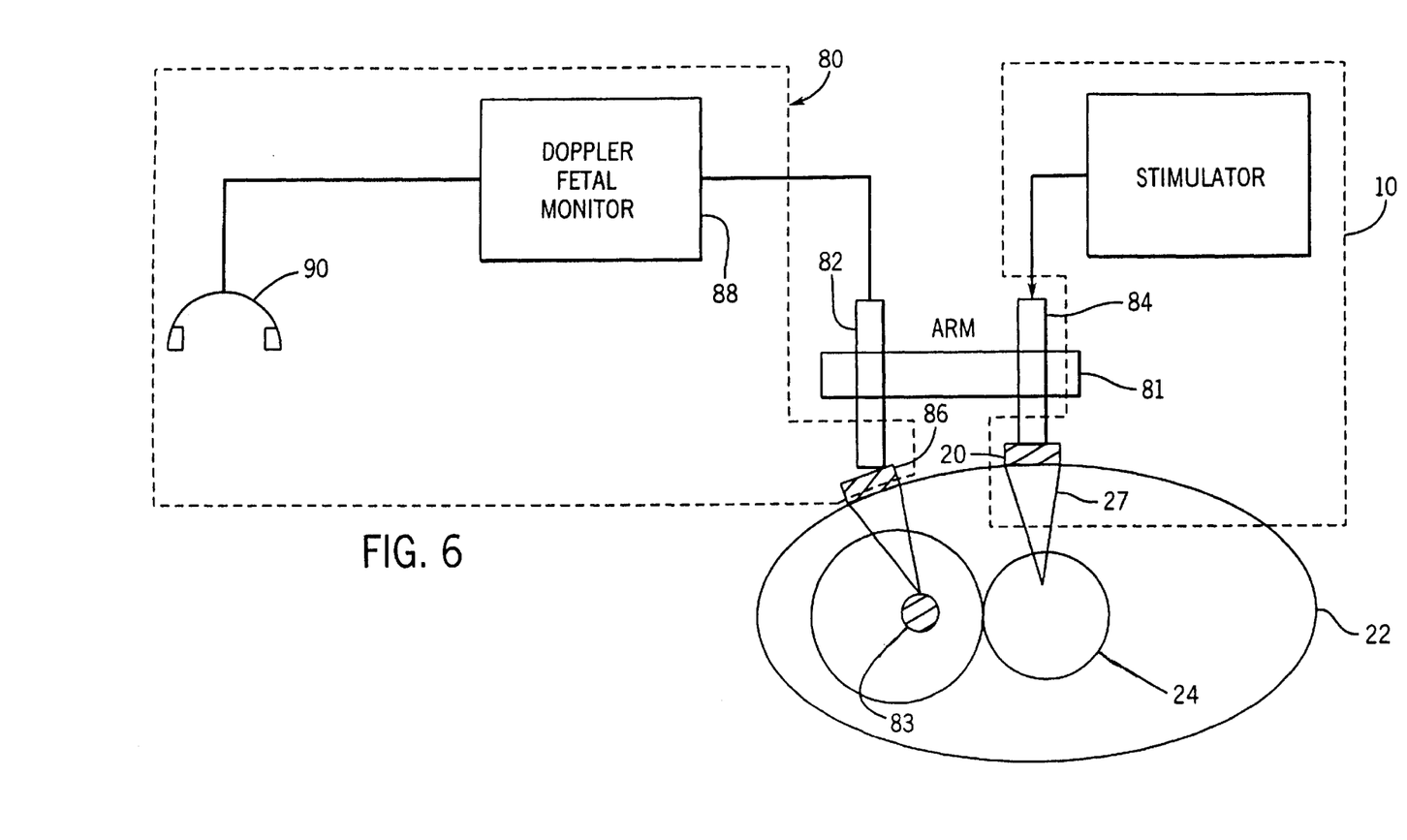
FIG. 6 is a block diagram of a fetal audio stimulator and association monitoring device constructed in accordance with another embodiment of the invention.

Referring now to FIG. 6 a fourth embodiment of a fetal audio stimulator 10 and associated monitoring device 80 is shown. In this application the transducer 20 is coupled to a first end of an arm 81 and the receiving transducer 86 is coupled to a second end of the arm 81. Each of the ultrasound transducer 20 and receiving transducer 86 are pivotally coupled to the arm 81 via pivoting members 82 and 84 which allow the transducers to be directed at a specific portion of the fetus. The receiving transducer 86 is coupled to a Doppler fetal monitor 88 and associated earphone 90 which is used to locate the heart 83 of the fetus while the transducer 20 is directed at the head of the fetus as described above.

In the embodiment of FIG. 6, the Doppler fetal monitor 88 produces a narrow beam, low-power, Doppler ultrasound beam that is used to detect fetal heart motion. This system is designed to locate the position of fetal heart with high accuracy, and in contrast to conventional Doppler fetal heart monitors, the ultrasound beam of this system is narrow and is focused on the fetal heart. The ultrasound power of the heart locator is set below the fetal stimulation level, hence it has no effect on the fetus.

Figure 7:
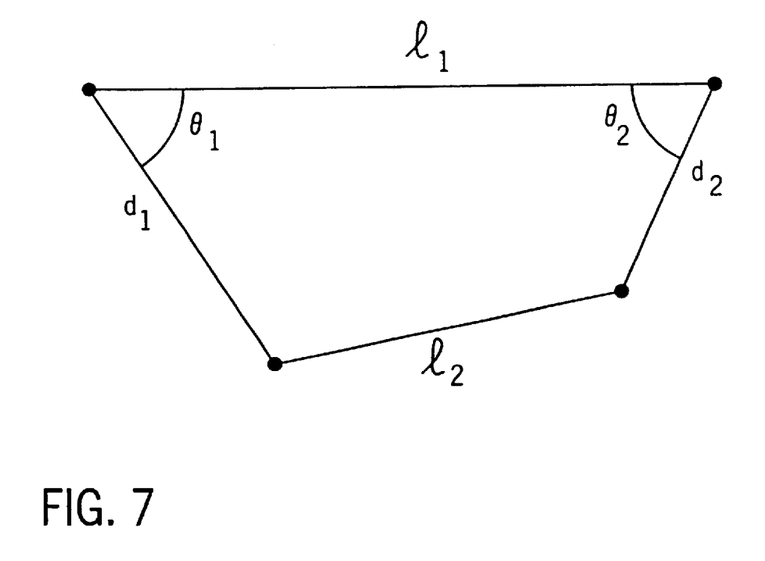
FIG. 7 is a graph illustrating the calculation of the distance between the heart and ear of a fetus for use in conjunction with the embodiment of FIG. 6.

The length of the arm 81 is approximately equal to the typical distance from the fetal heart to its head. To operate this device, the physician first searches for the fetal heart 83 by aiming the receiving transducer 86 at the fetus and receiving a response from the fetal monitor 88, for example through a set of earphones 90. Once the fetal heart has been identified by the fetal monitor 88, the physician orients the arm 81 in the direction of fetal head. Then, the ultrasound transducer 20 is oriented at an angle selected such that the distance between the focal points of the receiving transducer 86 and ultrasound transducer 20 is approximately equal to the heart-to-ear distance of an average fetus, at the age of the fetus being tested. Referring now to FIG. 7 given the length of the arm 81 ($l_1$) the focal length of the receiving transducer 86 ($d_1$), and the focal length of the ultrasound transducer 20 ($d_2$), the distance between the fetal heart and fetal head ($l_2$) can be calculated using simple geometry, thereby allowing a physician or other user to calculate and track the position of the fetal ear for purposes of applying a hearing or other test. Once the transducers are adjusted for the fetus, therefore fetal movement is tracked by the fetal heart monitor, and consequently the position of fetal ear can be tracked.

Each of the fetal audio stimulators 10 and 11 and associated monitoring devices described above can be used for stimulating and monitoring a fetus in clinical applications. In particular, the present invention can be used as a positioning device for positioning the fetus in the womb, or as an analysis device for assessing general health or hearing of the fetus.

One application for the fetal audio stimulators 10 and 11 is in fetal positioning. In this application, the localized source of fetal auditory stimulation is directed at the head 24 of the fetus to produce a stress to the fetus. The stressed fetus tries to avoid the stimulation by moving its head out of the stressful region, and hence assumes a new position. By moving the ultrasound transducer 20 or successively directing the ultrasound transducer 20 at selected locations on the fetus, a physician or other user can guide the fetus to a desired location in the uterus. Because fetal position before and during labor is critical, one clinical application of this device is to drive the fetus to the proper position in the uterus before labor. Another application is to use the fetal stimulation device 10 or 11 to position the fetus in a selected position before performing a diagnostic procedure on the fetus. For example, physicians can use the fetal audio stimulator 10 or 11 to move the fetus to a proper position before sonography or a maternal examination. Motion of the fetus can be monitored using any of the techniques described above, through imaging techniques, or in other ways known to those of skill in the art.

A second application of the fetal audio stimulators 10 and 11 is in assessing fetal health. The fetal audio stimulators 10 and 11 described above may be used to assess fetal health by stimulating the fetus and evaluating its response to the stimulation. Fetal response again may be detected and recorded in a number of ways, including any of the methods described above and through ultrasound imaging device. The fetal audio stimulators 10 and 11 presented here may also be integrated as a part of a fetal assessment test, such as the Biophysical Profile Test.

Another application of the fetal audio stimulators 10 and 11 is to increase fetal heart rate. Fetal heart rate can be detected and monitored by a number of methods such as Doppler fetal heart rate monitor, a stethoscope, an ECG recording device, or ultrasound imaging.

The fetal audio stimulators 10 and 11 and associated motion detection devices 40, 60, and 80 can also be applied in fetal hearing tests. The fetal audio stimulators 10 and 11 of the present invention are particularly suited for fetal hearing testing, in that they provide the opportunity to test fetal hearing at each ear separately. The directed beam 27 produced by the ultrasound transducer 20 is effective on strong reflectors such as the middle ear bones, and can therefore be directed to the middle ears of a fetus bypassing the external ear and the eardrum. Fetal movements in reaction to the stimulation, as detected in any of the ways described above or through ultrasound imaging, or in other ways known to those of skill in the art, provides an indication of the hearing capabilities of the fetus. During these tests, the frequency selector 26 can be used to vary the audio level, thereby providing testing of the hearing range.

Figure 8:
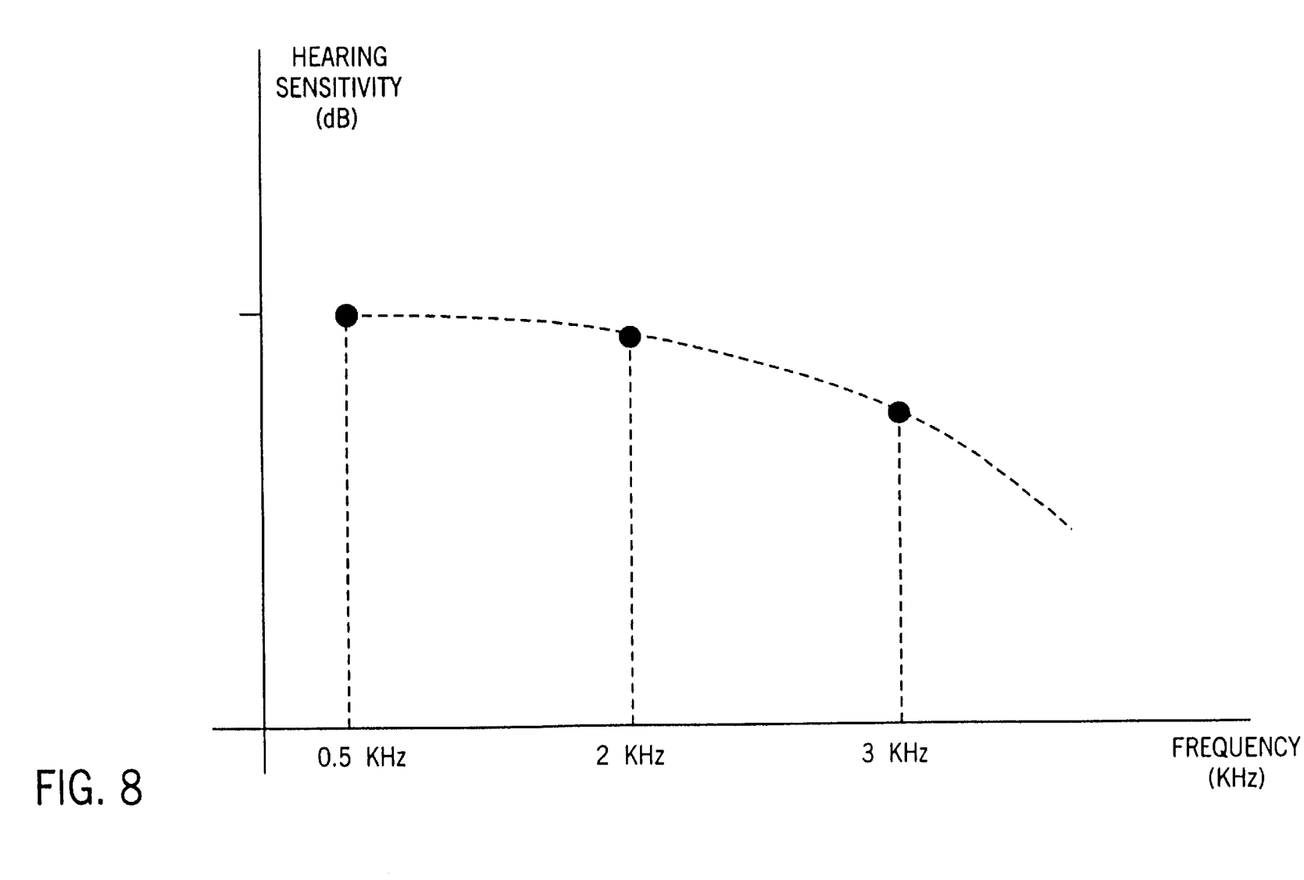
FIG. 8 is a typical audiogram developed for a single ear of a fetus.

Fetal hearing of each individual ear of a fetus can also be tested at different audio frequencies by changing the frequency of the audio generator 14 using the frequency selector switch 26, and then evaluating the lowest sound intensity to which the fetus responds. By this method it is possible to produce an audiogram, for individual ears of the fetus, similar to the conventional audiograms that are obtained in audiology clinics for adult patients. An illustration of the results of a typical test is shown in FIG. 8, wherein hearing sensitivity in decibels is charted versus frequency in kilohertz.

Although preferred embodiments of the present invention have been shown and described, it will be apparent to those of ordinary skill in the art that the present invention can be implemented in various ways. For example the excitation signal for the ear stimulation transducer can be in the form of a pulse train instead of an amplitude modulated sine wave. In this case, the modulation unit can be deleted. The resulting sound would not be single tone in this case, and would have harmonics that are multiples of pulse repetition frequency. Furthermore, although various combinations of fetal audio stimulation devices and associated monitoring methods have been shown, it will be apparent that various features of each of these embodiments can be combined to provide variations of the embodiments shown. Furthermore, although specific applications have been described, it will be apparent that fetal audio stimulation devices can be applied in a number of applications in which it is desirable to stimulate a fetus or to cause a fetus to move or increase its heart rate.

It should be understood, therefore, that the methods and apparatuses described above are only exemplary and do not limit the scope of the invention, and that various modifications could be made by those skilled in the art that would fall under the scope of the invention. To appraise the public of the scope of this invention, the following claims are made.

What is claimed is:

1. A stimulation device for stimulating hearing in a middle ear of a fetus in utero, the stimulation device comprising:
   an RF generator generating a carrier signal;
   an audio generator generating an audio range signal;
   an amplitude modulator, electrically coupled to receive the carrier signal from the RF generator and the audio range signal from the audio generator, the amplitude modulator being operable to modulate the carrier signal with the audio range signal to produce a modulated stimulation signal; and
   an ultrasound transducer electrically coupled to receive the modulated stimulation signal and being operable to convert the signal to a focused beam;
   wherein the ultrasound transducer is adapted to be acoustically coupled to the fetus and positioned to direct the focused beam at an ear of the fetus to stimulate hearing and movement.

2. The apparatus as defined in claim 1 further comprising an amplifier electrically coupled between the amplitude modulator and the ultrasound stimulation transducer.

3. The apparatus as defined in claim 2, further comprising an amplitude control potentiometer electrically coupled in a feedback loop of the amplifier.

4. The apparatus as defined in claim 1, further comprising:
   a gate electrically coupled to receive the modulated signal from the amplitude modulator and to provide the modulated signal to the ultrasound transducer; and
   a gate control switch, the gate control switch being selectively activated to activate the gate, wherein the modulated signal is provided to the ultrasound stimulation transducer.

5. The apparatus as defined in claim 1, further comprising a frequency selector switch electrically coupled to the audio generator, the frequency selector switch being activated to select between a plurality of audio range signals.

6. The apparatus as defined in claim 1, further comprising:
   a demodulator circuit electrically coupled to receive the modulated signal from the amplitude modulator, the demodulator circuit producing a demodulated audio signal; and
   an earphone, electrically coupled to receive the demodulated audio signal from the demodulator circuit, wherein the audio signal produced by the earphone can be monitored by a user to determine when the fetus is being stimulated.

7. The apparatus as defined in claim 1, further comprising:
   a strip chart recorder; and
   a strip chart marker switch electrically coupled to the strip chart recorder, the strip chart marker switch being selectively activated to provide an indication to the strip chart recorder when a motion of the fetus is detected.

8. The apparatus as defined in claim 1 further comprising:
   a fetal monitor probe acoustically coupled to the fetus; and
   a Doppler fetal monitor electrically coupled to receive a signal indicative of motion from the fetal monitor probe.

9. The apparatus as defined in claim 8, further comprising:
   a strip chart recorder; and
   a chart marker, the chart marker being electrically coupled to receive a signal indicative of fetal motion from the Doppler fetal monitor and to provide a signal indicative of fetal motion to the strip chart recorder when a fetal motion event is detected.

10. The apparatus as defined in claim 1, further comprising:
    a receiving transducer;
    a mixer circuit, electrically coupled to receive the modulated signal from the amplitude modulator and to receive a reflected signal from the receiving transducer; wherein the mixer circuit down mixes the modulated and reflected signals to produce a down-mixed signal; and
    a low pass filter electrically coupled to receive the down-mixed signal from the mixer circuit, the low pass filter filtering the down-mixed signal to produce a Doppler shift signal indicative of a movement of the fetus.

11. The apparatus as defined in claim 10, further comprising a monitor for monitoring the Doppler shift signal.

12. The apparatus as defined in claim 11, wherein the monitor is a video monitor.

13. The apparatus as defined in claim 11, wherein the monitor is an audio monitor.

14. The apparatus as defined in claim 1, further comprising:
    an arm having a first end and second end, the ultrasound transducer being pivotally coupled to the first end of the arm wherein the ultrasound transducer is adapted to be selectively directed at the head of the fetus;
    a receiving transducer, the receiving transducer being pivotally coupled to the second end of the arm, wherein the receiving transducer is adapted to be selectively directed at the heart of the fetus; and
    a Doppler fetal monitor electrically coupled to receive a signal indicative of a motion of the fetus from the receiving transducer.

15. A method for producing a localized sound in a maternal abdomen, the method comprising the following steps:

generating a carrier signal in an ultrasound range;

modulating the carrier signal with an audio range signal to produce a modulated signal;

applying the modulated signal to an ultrasound stimulation transducer to produce a focused beam; and acoustically coupling the ultrasound stimulation transducer to the abdomen and directing the focused beam at a head of a fetus in utero, wherein a resultant force vibrates the middle ear of the fetus in the audio range.

16. The method as defined in claim 15, further comprising the step of applying the modulated signal to a demodulator to produce a demodulated audio signal.

17. The method as defined in claim 16, further comprising the steps of:

monitoring the demodulated audio signal;

monitoring motion of the fetus; and correlating the motion of the fetus with the demodulated audio signal.

18. The method as defined in claim 15, further comprising the step of detecting audio-induced motion of the fetus with a Doppler motion detector.

19. The method as defined in claim 15, further comprising the steps of:

focusing a receiving transducer for detecting signals in the same frequency range as the audio range signal at the same location as the ultrasound stimulation transducer; and monitoring a reflected signal to detect a Doppler shift indicative of motion of the fetus.

20. The method as defined in claim 15, further comprising the steps of:

pivotally mounting the ultrasound stimulating transducer to a first end of an arm;

pivotally mounting a receiving transducer to the second end of the arm;

coupling the receiving transducer to a fetal monitor, monitoring a heart beat of the fetus with the fetal monitor, tracking fetal movement with the fetal monitor; and correlating the motion to a location of the fetal ear.

21. The method as defined in claim 20, further comprising the step of determining the orientation angle of the stimulation transducer by evaluating a heart to ear distance, a focal length of the ultrasound transducer, a focal length of the receiving transducer, and a length of the arm.

* * * * *

UNITED STATES PATENT AND TRADEMARK OFFICE
CERTIFICATE OF CORRECTION

PATENT NO. : 6,709,407 B2
DATED : March 23, 2004
INVENTOR(S) : Mostafa Fatermi

It is certified that error appears in the above-identified patent and that said Letters Patent is hereby corrected as shown below:

Column 1,
Lines 55 and 56, "a modulation" should be -- an audio --.

Signed and Sealed this

Thirteenth Day of July, 2004

JON W. DUDAS
*Acting Director of the United States Patent and Trademark Office*